US012723000B2

(12) United States Patent
Krüger et al.

(10) Patent No.: US 12,723,000 B2
(45) Date of Patent: Sep. 1, 2026

(54) TWO-PART REACTION VESSELS MADE OF GLASS, PRODUCTION METHOD AND ANALYTICAL METHOD

(71) Applicant: LPKF LASER & ELECTRONICS AG, Garbsen (DE)

(72) Inventors: Robin Krüger, Hannover (DE); Malte Schulz-Ruhtenberg, Wunstorf (DE); Jan Van Aalst, Garbsen (DE); Moritz Woller, Neustadt (DE)

(73) Assignee: LPKF LASER & ELECTRONICS AG, Garbsen (DE)

( * ) Notice: Subject to any disclaimer, the term of this patent is extended or adjusted under 35 U.S.C. 154(b) by 722 days.

(21) Appl. No.: 17/774,959

(22) PCT Filed: Nov. 10, 2020

(86) PCT No.: PCT/EP2020/081592
§ 371 (c)(1),
(2) Date: May 6, 2022

(87) PCT Pub. No.: WO2021/094290
PCT Pub. Date: May 20, 2021

(65) Prior Publication Data
US 2022/0388896 A1 Dec. 8, 2022

(30) Foreign Application Priority Data
Nov. 12, 2019 (DE) ......................... 102019217466.3

(51) Int. Cl.
*C03C 15/00* (2006.01)
*C03C 23/00* (2006.01)
(Continued)

(52) U.S. Cl.
CPC .......... *C03C 15/00* (2013.01); *C03C 23/0025* (2013.01); *C03C 27/06* (2013.01); *C12M 23/22* (2013.01)

(58) Field of Classification Search
CPC .... C03C 23/0025; C03C 15/00; C12M 23/22; C03B 23/20
See application file for complete search history.

(56) References Cited

U.S. PATENT DOCUMENTS

2003/0211014 A1 11/2003 Jacquorie et al.
2005/0142812 A1 6/2005 Kurosawa
(Continued)

FOREIGN PATENT DOCUMENTS

EP 1867612 A1 12/2007
EP 2011857 A1 1/2009
JP 200531774 A 12/2005

OTHER PUBLICATIONS

Deutsch et al., "A novel miniature cell retainer for correlative high-content analysis of individual untethered non-adherent cells", Lab Chip, 2006, pp. 995-1000, vol. 6, The Royal Society of Chemistry.
(Continued)

*Primary Examiner* — Erin Snelting
(74) *Attorney, Agent, or Firm* — Greer, Burns & Crain, Ltd.; Steven P. Fallon

(57) ABSTRACT

The invention relates to a method for producing reaction vessels from glass and to the glass reaction vessels obtainable by this method. The method comprises the following steps: 1. irradiating the surface of a first glass sheet by means of a laser beam of a wavelength for which the first glass sheet is permeable, 2. etching the first glass sheet to form
(Continued)

Figure 1:
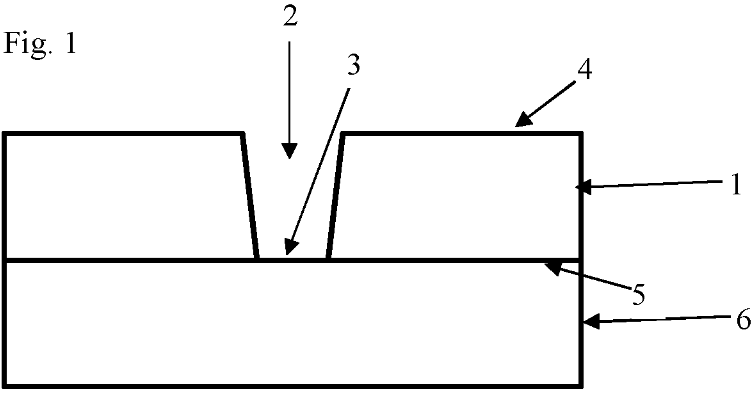

recesses that extend over the complete thickness of the first glass sheet, and 3. connecting a second sheet with a surface of the first glass plate.

15 Claims, 4 Drawing Sheets

(51) Int. Cl.
*C03C 27/06* (2006.01)
*C12M 1/00* (2006.01)

(56) References Cited

U.S. PATENT DOCUMENTS

2009/0013724 A1 1/2009 Koyo et al.
2009/0075805 A1* 3/2009 Kurachi ................ B01L 3/5085 501/59
2014/0116091 A1* 5/2014 Chuang ................... C03C 15/00 65/31
2017/0352553 A1 12/2017 Bellman et al.
2018/0005922 A1* 1/2018 Levesque, Jr. ........ H10P 50/283
2019/0055510 A1* 2/2019 Lee .................... G01N 33/5011
2021/0230060 A1* 7/2021 Magalhães Mendes ..................... C03C 27/046
2022/0204393 A1* 6/2022 Noda .................. B23K 26/402
2022/0347796 A1* 11/2022 Liu .................... G02B 27/0938

OTHER PUBLICATIONS

International Search Report and Written Opinion from the corresponding International Patent Application No. PCT/EP2020/081592, dated Jan. 29, 2021.

Wittmann-Regis, Agnès, “International Preliminary Report on Patentability”, May 17, 2022.

* cited by examiner 2
3
4
1
5
6

2
3
Z a)
b)
1
2
3
4
5
6
7
8
9
10
25 a)
b)
c)
2
3
6
11
12
13
14
13, 14
24
25 b)

a)
b)
c)
1
2
2'
6
7
10
15
16
17
18
20
21
22
23
25

1
6
19
Z
19
2

TWO-PART REACTION VESSELS MADE OF GLASS, PRODUCTION METHOD AND ANALYTICAL METHOD

The present invention relates to a method of producing glass reaction vessels formed in the form of recesses in glass. The glass in which the reaction vessels are formed in an array comprises two or more than two interconnected glass elements, optionally directly connected to each other or by means of a connecting layer disposed between the glass elements. The method produces an arrangement of a plurality of reaction vessels formed into glass, for example, a 25×25 array of 8×12 reaction vessels each. The reaction vessels are generated in a plurality in a glass plate, which may consist of a first glass plate and a second glass plate tightly connected thereto, or further glass plates connected in the same manner.

The method has the advantage of forming recesses without mechanical action on a solid glass, forming reaction vessels that therefore have no mechanical damage, e.g. no microcracks. The reaction vessels have a large aspect ratio of depth to diameter. Another advantage is that the method of producing the reaction vessels can proceed at least without selectively coating the surface of the glass in which the cross-sectional openings of the reaction vessels are formed, optionally without any coating of the surfaces of the glass in which the reaction vessels are formed.

State of the art

Deutsch et al., Lab Chip, 2006, 69, 995-1000, describe the production of reaction vessels of a diameter of 20 μm at 8 μm depth in a glass plate by etching after applying a mask of chromium and photoresist thereon.

US 2003/0211014 A1 describes the production of reaction vessels in glass by means of a tool exposed to ultrasound and abrasives between the tool and the glass.

EP 1 867 612 A1 describes microtiter plates with 96 wells made of a bottom of glass that is permeable to UV and connected by glass frit to a glass plate in which continuous recesses form the side walls of the wells.

EP 2 011 857 A1 describes the creation of surface structures on the bottom of microtiter plates by means of a photolithographic process.

Object of the Invention

The invention has the object of providing an alternative production method which is particularly suitable for producing reaction vessels with a large aspect ratio at an overall small volume in glass, as well as providing an arrangement of a plurality of such reaction vessels in glass. Preferably, the method shall be suitable to provide an arrangement of such reaction vessels in which the glass forms a high optical contrast to cells in the reaction vessels when irradiated with light.

DESCRIPTION OF THE INVENTION

The invention achieves the object by the features of the claims and, in particular, by a method for producing reaction vessels made of glass as well as the reaction vessels made of glass obtainable by the method. The method comprises and consists of the steps of 1. irradiating, preferably point-like irradiating, a laser beam of a wavelength for which the first glass plate is transparent, onto the locations of the surface of a first glass plate at which a recess each is to be produced as a reaction vessel,
2. etching the first glass plate, preferably for a time sufficient to produce recesses of a depth, preferably of at least 40 μm or at least 30 μm, preferably with an aspect ratio of at least 2, at least 4, at least 5, or at least 6 of depth to diameter measured in the plane of the first surface, along the locations to produce recesses extending through the full thickness of the first glass sheet,
3. after etching the first glass plate to form recesses, connecting a second plate to a surface of the first glass plate.

Herein, each glass plate here can be an object made of glass with a lateral extent greater than its thickness. Glass plates can thus have a rectangular, round or otherwise shaped perimeter that limits their opposing surfaces.

The reaction vessels are formed by recesses in a first glass plate, the recesses having precisely one opening lying in the plane of a first surface of the first glass plate. Applications of the reaction vessels are not limited to chemical reactions, but include biochemical, biological, and physical processes. These may be processes involving single cells, which may be animal or plant cells or yeast cells, bacteria, viruses, proteins, etc., or clusters thereof.

The punctiform irradiation is achieved by focusing the laser irradiation on a point with a size of a few micrometers, e.g. 1 to 10 μm or up to 5 μm. Therein, it is advantageous that the focus of the laser irradiation extends over a length along the direction of propagation of the laser beam that is substantially greater than the Rayleigh length of a corresponding laser beam with a Gaussian profile. This can be achieved by suitable optical devices, e.g. diffractive optical elements. The irradiating may be an irradiating through, or an irradiating may be performed less deeply into a first thickness portion of the first glass plate adjacent to the first surface, e.g. in that the focus of the laser radiation in the direction of the propagation direction of the laser irradiation does not extend over the entire thickness of the glass plate. Since an interaction between the laser radiation and the material of the glass plate takes place only in the focus, it is thus possible to let the interaction area end within the first glass plate. Preferably, the laser irradiation consists of laser pulses.

Therein, when connecting a second glass plate to a surface of the first glass plate, the surface of the first glass plate may be the first surface of the first glass plate onto which the laser beam was irradiated or the second surface opposite to this first surface.

The first surface of the first glass plate, and in the absence of a coating of etch resist also the second surface opposite to it, is removed significantly faster during etching at the locations in which the laser was irradiated onto the first glass plate and where the laser beam exited opposite to it, than the neighboring areas. Therefore, the areas of the first surface and, if necessary, the second surface of the first glass plate are removed more slowly and uniformly at a distance from the locations of punctiform laser irradiation because of the absence of a coating, e.g. of etching resist. Therefore, except for the recesses, the first surface is formed by surface sections arranged in a plane from which the recesses extend into the glass volume of the first glass plate. The surface sections arranged in a common plane and forming the first surface from which the recesses are worked-off are formed by the end faces of the walls located between the recesses. In the absence of a coating from the second surface opposite to the first surface, the recesses may also extend into the glass volume starting from the second surface along the locations where the laser beam has been irradiated or transmitted in a punctiform manner. Therein, recesses can be formed which have an hourglass-shaped longitudinal section through the thickness of the glass plate.

In step 2, etching is performed for a time sufficient to form recesses that extend through the full thickness of the first glass sheet so that the depth of the recesses is equal to the thickness of the first glass sheet.

Optionally, the punctiform irradiated laser beams in step 1, at which a recess to form a reaction vessel is etched in step 2, are arranged in the plane of the first surface of the first glass plate at a distance of at least or exactly the diameter of one of the reaction vessels plus the thickness of a wall between the reaction vessels. The diameter of the reaction vessels is adjustable through the reaction conditions and the duration of the etching, since the etching is concentric about the linear path taken by the irradiated laser beam through the first glass plate. The walls located between the reaction vessels end in a common plane. The end faces of these walls lie in a common plane and form the first surface or form the first surface in a common plane, the first surface being interrupted by the recesses. Preferably, the first surface is interrupted only by the cross-sections of the recesses.

The laser beam is preferably pulsed at each of the locations where it is irradiated onto the first glass plate, e.g. with a wavelength of 1064 nm, preferably with pulse lengths of at most 100 ps or at most 50 ps, preferably at most 10 ps. Generally, the laser is arranged so that the laser beam does not strike the first glass plate between locations. Preferably, the laser beam is irradiated in a punctiform manner and perpendicularly onto the surface of the first glass plate. Preferably, this surface onto which the first laser beam has been irradiated forms the first surface of the first glass plate.

The etching is carried out, e.g. with hydrofluoric acid, e.g. 1 to 48 wt. %, and/or sulfuric acid and/or hydrochloric acid and/or phosphoric acid and/or nitric acid, or potassium hydroxide solution, at e.g. up to 140° C.

The first glass plate e.g. may have a thickness before etching of up to 1000 μm, preferably 100 to 1000 μm, e.g. up to 800 μm, e.g. 300 to 500 μm, and a thickness after etching that is smaller by 50 to 700 μm less, e.g. smaller by up to 200 μm.

The recesses preferably extend at an angle of, for example, 0° to 15° in a conical or frustoconical manner and extend starting from the surface of the first glass plate into its volume.

In the embodiment according to the invention, in which the recesses extend through the first glass plate and a second glass plate is connected to the first glass plate, the second surface of the first glass plate can optionally be coated with etch resist. Therein, the second surface of the first glass plate lies opposite to its first surface onto which the laser beam was directed, or through which the laser beam impacted into the first glass plate. Optionally, the etch resist can be applied over the entire surface of the second surface of the first glass plate after or before irradiating the laser beam.

Optionally, in general, the first glass plate may be subjected to etching without a coating, e.g. without a mask and/or without etch resist, so that the process has the advantage of being performed without applying and without removing etch resist from a glass plate. Generally, at least the first surface of the first glass plate remains without etch resist and without mask and is etched without etch resist.

Generally optionally, each location of the first glass plate where a recess is to be created may be irradiated in a punctiform manner with laser beams at a plurality of spaced positions, e.g. at least 3 or at least 10 or at least 30 positions, the laser beams preferably being irradiated in parallel to each other and in perpendicular to the first glass plate, subsequentially or simultaneously. The positions form the location at which the etching removes the first glass plate faster than at surface areas spaced therefrom. The positions at which the laser was irradiated lead to a uniformly fast removal of the glass during etching and together form a recess. The positions that are irradiated in the area of a location and form a location are arranged, e.g. at a distance of 1 to 10 μm. Preferably, the positions are arranged within the area around each location where a recess is to be formed in each case. Preferably, the positions at which laser beams are irradiated around a location or to form a location are arranged at a distance of 1 to 10 μm, e.g. 2 to 5 μm or up to 3 μm, which is determined in particular in the plane of the first surface of the first glass plate.

In general, a recess can be created by a single laser pulse or multiple laser pulses. In the case of a single laser pulse, the diameter of the recess is determined primarily by the etching time. When a recess is created with multiple laser pulses, the diameter of the recess is determined by the number and spacing of positions at which laser beams are irradiated for a location and penetrate the first glass plate. The depth of the recess in the volume of the first glass plate can be determined by the time duration of etching and by the laser beam penetrating only a portion of the first glass plate or does not completely irradiate through the first glass plate.

Optionally, around each location where a recess is to be formed, a laser beam is irradiated on a circumferentially closed path, which is preferably annular, rectangular or hexagonal, which is formed, for example, by laser beam pulses irradiated next to each other. Therein, laser beam pulses can be irradiated onto the first glass surface along the circumferentially closed path, e.g. at a spacing of the laser beam pulses of 3 μm next to each other determined on the first surface of the first glass plate. Optionally, therefore, the first glass plate may be irradiated with laser beams at each location at a plurality of positions spaced apart from each other in a punctiform manner, respectively, and a laser beam, e.g. formed by laser beam pulses irradiated side by side, may be irradiated around these positions along a circumferentially closed path. Irradiating a laser beam along a circumferentially closed path has the advantage that, during subsequent etching, recesses are formed with a wall that extends from the first surface and has a cross section that includes the circumferentially closed path.

In general, laser pulses can be irradiated to different depths into the first glass plate at positions that form a location where a recess is formed by etching. For example, laser pulses at positions can be irradiated more deeply and penetrate deeper into the thickness of the first glass plate, and other laser pulses at positions can be irradiated less deeply into the thickness of the first glass plate. During subsequent etching, deeper or more recesses are formed at positions where laser pulses were irradiated more deeply into the glass plate, and the bottom of the recess is formed at a lesser depth at positions where laser pulses were irradiated less deeply into the glass plate. In general, depending on the spacing of the positions, a concave recess can be formed in the bottom at each position. A recess having a bottom and further deeper recesses therein can be produced by irradiating laser pulses less deeply into the first glass plate in the share of the positions that are to form the bottom, and irradiating laser pulses more deeply into the first glass plate in the share of the positions that are to form further recesses extending from the bottom deeper into the first glass plate and subsequent etching. For a larger diameter of further recesses extending deeper into the first glass plate starting from the bottom of a recess, laser pulses irradiated deeper into the first glass plate can be arranged at adjacent positions, e.g. at a distance of 1 to 10 µm, e.g. 2 to 5 or up to 3 µm, so that at these positions the etching penetrates deeper into the first glass plate. Thus, laser pulses may be irradiated, less deeply into the first glass plate at a share of the positions, and laser pulses may be irradiated more deeply into the first glass plate at a share of the positions, so that etching at the positions where the laser pulses have been irradiated less deeply produces a bottom with concave recesses at a lesser depth, and at the positions where laser pulses have been irradiated more deeply produces further recesses extending more deeply into the first glass plate.

In a further embodiment, e.g. a method consisting of steps 1 to 3, the reaction vessels are formed by recesses extending through the full thickness of the first glass plate, wherein a second plate is connected to a surface of the first glass plate. The second plate forms the bottom of the reaction vessels. Therein, the second plate may be connected to the first surface, preferably the second surface, of the first glass plate. The arrangement of the second plate to the second surface of the first glass plate forms reaction vessels that taper conically from their opening, which is in the plane of the first surface of the first glass plate, to the second glass plate and therefore optionally do not form an undercut. The second plate is preferably a second glass plate and is therefore optionally also referred to generally as a second glass plate by way of representation for second plates of other material. The second plate may be a glass plate or may comprise or consist of silicon, sapphire, ceramic, metal, or at least two layers thereof.

Therein it is preferred that the second surface of the first glass plate is fully coated with etch resist to allow etching to act only from the first surface. The coating of the second surface results in the formation of recesses that extend cylindrically or conically from the first surface in the direction towards the second surface and prevents etch removal from the second surface. In this embodiment, etching can generally be allowed to act exclusively on the first surface of the first glass plate until the recess extends into the plane of the second surface of the first glass plate. It has been found that when the second surface is coated with etch resist, the etching produces recesses through the entire thickness of the first glass plate, the wall of which is perpendicular or at the angle of the cone shape or frustocone shape to the plane of the second surface, preferably without a transition arc and/or without chamfer from the wall of the recess to the second surface. In this embodiment, etching causes the recess to taper cylindrically or at the same angle down to the plane of the second surface.

The reaction vessels have e.g. a depth of at least 40 µm, at least 50 µm or at least 100 µm or at least 150 µm, e.g. up to 250 µm or up to 200 µm. The reaction vessels have, for example, a diameter of at least 10 µm or at least 30 µm, e.g. up to 200 µm or up to 1 mm, generally preferably with an aspect ratio of depth to diameter of at least 2, at least 4, at least 5 or at least 6. The recesses of the first glass plate have, for example, an internal volume within the first glass plate of from 1 pL to 1 µL.

The connecting of the second plate, which is in particular a second glass plate, to the first glass plate, preferably to the second surface of the first glass plate, can be performed by placing the first and second plates directly on top of each other with subsequent heating, e.g. in the case of quartz glass to 400 to 1200° C. Therein, the connecting can be carried out at longer duration and lower temperature, or higher temperature and shorter duration of the connecting process, the temperature depending on the maximum temperature at which the first glass plate and the second plate are still sufficiently dimensionally stable. Alternatively, glass frit, a paste containing a proportion of glass particles which has a lower melting point than the first glass plate and than the second plate, is arranged between the first and second glass plates and the glass plates are connected by heating to a temperature at which the glass frit softens or melts. Preferably, the glass frit is applied to the second surface of the first glass plate or the first surface of the second glass plate, for example, by screen printing or dispensing printing with subsequent placing of the second glass plate against the first glass plate and heating.

Optionally, the glass frit is colored, e.g. with a content of glass particles that, when used in the irradiation of light in a wavelength range of light, have a lower transmission than the second glass plate. E.g. the glass frit, in particular the glass particles contained therein, may contain metal oxides such as iron oxide, magnetite, titanium dioxide, mixed oxides, e.g. cobalt aluminate, spinel, e.g. iron chromium spinel, or a mixture of at least two of these. Reaction vessels formed into a first glass plate with their bottoms formed directly by a second glass plate connected to the first glass plate by colored glass frit have the advantage that upon irradiating light and detection for analysis, interactions due to radiation passing through the region of the first and second glass plates adjacent the reaction vessels are reduced.

When the first glass plate is coated with an etch resist on the second surface after laser irradiation and subsequently etched, recesses with a conical cross-section are typically formed. The etching process is typically stopped for the embodiment in which the recesses are formed continuously when continuous recesses of a desired diameter are formed by the first glass plate. Depending on the choice of material of the etch resist, this can result in a detachment of the etch resist and a so-called under-etching. Therein, the area of the second surface around the recess is also attacked by the etching medium, whereby the etching process continues along the contact surface of the glass plate and etch resist and the etch resist is further detached. Thus, around the recess, the thickness of the first glass plate is reduced and a circumferential chamfer, also referred to as a transition arc, under-etching or undercut, is created at the recess adjacent to the second surface. In the subsequent connecting process, this can lead to the formation of gaps between the first glass plate and the second plate. These gaps can be closed by applying pastes containing glass frit and then melting the glass frit. Therefore, in such cases, joining the glass plates with glass frits is particularly advantageous. Such a chamfer can be filled by glass frit when glass frit is arranged over the entire surface of a second glass plate, which is arranged against the second surface of the first glass plate and connected thereto. It is also possible, in the case of a chamfer extending from the recess to the second surface of the first glass plate, to apply glass frit to this second surface, for example uniformly, in particular by means of screen printing, and to arrange a second glass plate against it. In this embodiment, the chamfer can receive glass frit so that the bottom of the reaction vessel covering the clear cross-section of the recess is formed only by the second plate. Therefore, the bottom of the recess may remain recessed from glass frit paste so that the bottom is still formed by the surface of the second plate. Alternatively, the glass frit paste may also cover the bottom. This can be advantageous because during the connecting process, the glass frit is melted and then has a surface tension that can lead to the formation of a glass lens disposed on the second plate, each forming the bottom of individual reaction vessels. This effect can be advantageous in illuminating the reaction vessel.

Alternatively, the second glass plate can be connected to the second surface of the first glass plate by anodic bonding. Therein, the second surface of the first glass plate and/or the surface of the second glass plate facing the first glass plate is coated with silicon, e.g. by means of cathode sputtering, also known as sputtering, the first glass plate is placed against the second plate and a voltage of e.g. 300-500 V is applied, and optionally heated, e.g. to 400° C. Thereby, the two glass plates are connected to each other by means of diffusion of ions (e.g. Na, K) and oxygen anions contained in the glass.

Alternatively, the glass plates can be joined by fusion bonding, preferably without an interlayer, by bringing one of the surfaces of the first glass plate into contact with one of the surfaces of the second glass plate and heating and applying pressure.

The same connection methods, or combinations of the methods, can be used to connect additional glass plates to the first and/or second glass plates.

Generally, heating can be performed in an oven.

Further generally, the second glass plate may consist of glass that is more reactive for chemical surface modification than the glass of the first glass plate. E.g. the second glass plate may consist of soda-lime glass, and the first glass plate of borosilicate glass, so that aqueous or organic reagents introduced into the reaction vessels will bind primarily to the glass of the second glass plate, which forms the bottom of the reaction vessels. Additionally or alternatively, the second glass plate may comprise a different glass composition than the first glass plate, e.g. the second glass plate may comprise quartz glass or fused silica, the first glass plate borosilicate glass.

Optionally, strip conductors may be applied to the surface of a second plate which is connected to a first glass plate, e.g. strip conductors which are arranged separately next to each other and which are connected to separate connection surfaces and can therefore be contacted separately from each other. Preferably, to connect the glass plates, glass frit in paste form is applied by screen printing to a surface of the first glass plate and the second glass plate is arranged to the surface to which the glass frit was applied, with subsequent heating.

In embodiments in which a first glass plate is connected to a second glass plate by means of a layer of molten glass frit lying between these, a first strip conductor may optionally be deposited on the first glass plate and a second strip conductor may optionally be deposited on the surface of the second glass plate facing the first glass plate. The first strip conductor preferably covers at least a portion of the recesses created in the first glass plate, optionally the first strip conductor fully covers the first surface and at least a portion of the recesses. The second strip conductor extends along the area forming the bottom of a reaction vessel, and is preferably connected to a contact surface disposed on a section of the second glass plate that projects over the first glass plate. The first and second strip conductors may be applied by sputtering or printing, the first strip conductor after etching, for example, and the second strip conductor before connecting the second glass plate to the first glass plate. Insulation between first and second strip conductors is formed by the layer of fused glass frit disposed between the first and second glass plates, particularly only in the area where the first and second glass plates are adjacent to each other, or excluding the areas where recesses are formed in the first glass plate. Optionally, recesses may be formed in the second glass plate in which recesses the second strip conductors are arranged. Such recesses may extend along the surface of the second glass plate facing the first glass plate. Such recesses may be formed e.g. by etching in the second glass plate, e.g. after irradiating the second glass plate along the path of such recesses, e.g. with pulsed laser beams irradiated alongside each other prior to etching. Alternatively, recesses may be created after photolithographic creation of an etch mask with subsequent etching and following removal of the etch mask. Such recesses may be formed, e.g. as ditches having a V-shaped or U-shaped cross-section. Material for strip conductors can be introduced into recesses, e.g. by means of a printing process. Preferably, strip conductors consist of metal, e.g. gold, silver, copper or mixtures of at least two of these.

The recesses formed in the first glass plate may have a larger cross-section in an upper thickness section than in a lower thickness section adjacent thereto, which is divided into at least two partial recesses, the lower thickness section being adjacent to the second plate, e.g. connected thereto directly or by means of a layer of molten and solidified glass frit. In this embodiment, the terminal cross-sectional openings of the at least two partial recesses adjacent to the second plate are covered by the second plate. The recesses extending across the upper thickness portion cover at least two partial recesses. Partial walls formed as a single piece from the first glass sheet over the lower thickness portion are disposed between the partial recesses extending over the lower thickness portion. These partial walls are spaced from each other around the partial recesses. These partial walls are formed by irradiating laser pulses that penetrate only maximally into the upper thickness portion of the first glass plate in the area of the partial walls, and irradiating laser pulses in the region of the partial recesses that penetrate completely through the first glass plate, and subsequent etching of the first glass plate. During etching, the recess formed in the upper thickness portion adjacent to the first surface of the first glass plate extends over the area of at least two partial recesses. The longitudinal central axes of the partial recesses may be spaced, e.g. from 10 up to 100 μm apart. The partial walls extend over the lower thickness section between the partial recesses, wherein the partial recesses may have a diameter of, e.g. 1 to 50 in the plane of the second surface of the first glass plate adjacent to the second plate. The upper thickness section is also referred to herein as the first thickness section, and the lower thickness section is also referred to as the second thickness section. The upper thickness section and the lower thickness section extend starting the first surface of the first glass sheet, independently of each other, e.g., up to at least 20% or at least 30% or at least 40% or at least 50%, e.g., up to 80% or up to 70% or up to 60% of the thickness of the original first glass sheet. Therein, the lower thickness section extends into the thickness of the first glass sheet to a greater extent than the upper thickness section. Generally, the thickness sections do not extend throughout the complete thickness of the first glass sheet. E.g. the first and in particular the second thickness section may be predetermined so that after etching in the area of the recess a thickness of the first glass plate, or between the recess and the second surface, of at least 5%, at least 10% or at least 15% or at least 20% remains.

A third plate may be disposed on the first surface of the first glass plate opposite the second plate, and connected to the first glass plate. The third plate has third recesses which extend through the complete thickness of the third plate and are arranged to fit, in particular to be aligned, over the recesses of the first glass plate. Therein, the third recesses may have a diameter equal to or greater than the diameter of the recesses of the first glass plate. Optionally, the third recesses may each extend over two or more recesses of the first glass plate. The third recesses are suitable for use, for example, as a funnel tube for filling the recesses in the first glass plate. E.g. the third recesses may have a volume of 0.01 to 10 μL, e.g. 0.1 to 3 μL, within the third plate.

In general, especially when a third plate is arranged at the first glass plate, the recesses in the first glass plate can each be arranged at a distance of their longitudinal central axes of 20 to 200 μm. During the production, the laser pulses passing through the first glass plate are generally irradiated at the spacing of the longitudinal central axes of the recesses, or resp. partial recesses. The recesses in the first glass plate may have a diameter of, for example, 5 to 200 μm in the plane of the second surface of the first glass plate.

The third plate may be a glass plate, e.g. of a thickness of at least 100 μm or at least 300 μm, e.g. up to 2000 μm or up to 1000 μm. The third recesses may have an inner diameter of, e.g., at least 0.2 mm or at least 0.5 mm, e.g., up to 3 mm or up to 2 mm or up to 1 mm. The third plate may be connected to the first glass plate by means of anodic bonding, by means of a molten and solidified layer of glass frit between the first glass plate and the third plate, e.g. applied by screen printing, or by means of fusion bonding.

Optionally, the second plate, particularly in the embodiment of a second glass plate, may have second recesses in the area where it covers the recesses formed in the first glass plate, the second recesses having a smaller diameter than the recesses of the first glass plate. Second recesses may be blind holes open to the first glass plate or may extend through the full thickness of the second plate in order to form a retaining device for larger particles. Second recesses may be formed in the second plate by the methods described with reference to forming recesses in the first glass plate. The second recesses may be conical in shape, preferably with their smaller diameter lying in the plane of the surface of the second plate which faces and is connected to the first glass plate. E.g., the second recesses may have diameters ranging from 1 μm to 50 μm in the plane of the surface of the second plate facing the first glass plate. Preferably, the recesses of the second plate have a diameter smaller by a factor of 5 to 10 than the diameter of a cell contained in the reaction vessel, e.g. recesses having a diameter of 1 to 3 μm, in particular of 1 or of 1.5 μm to 2 μm, e.g. for a cell diameter of 7 to 15 μm. E.g., the longitudinal central axes of the second recesses may be spaced from 10 to 100 μm apart. A second plate, which is preferably a second glass plate, preferably has a thickness in the range of 50 to 500 μm, e.g., up to 150 μm or up to 100 μm.

In this embodiment, the bottom of the recesses of the second glass plate may have microstructures arranged for near-field illumination of the inner volume of the recesses. Such microstructures may, e.g., be in the form of narrow, tall glass tips and thus be capable of acting as optical waveguides for illumination or of influencing the position or orientation of individual cells or collections of cells. Such structures can be made, e.g., by forming a recess by etching a plurality of positions onto which closely spaced laser pulses have been irradiated. If a single laser pulse is omitted at the center of the recess, a glass tip remains here within the recess after the etching process. In general, a recess can be created in the method by irradiating laser pulses next to each other at positions and subsequent etching, wherein the positions are arranged at equal distances from each other of at most 10 μm, e.g. 1 to 5 μm or up to 3 μm, and together form a location, wherein at least 2 or at least 3 positions are arranged at a greater distance, e.g. at a distance of 10 to 30 μm, e.g. 15 to 20 μm distance. The at least 2 or 3 positions of the laser pulses arranged at a greater distance between them have e.g. the area in which a laser pulse is omitted at the same distance, or surround the area in which a glass tip remains standing during etching.

In embodiments for producing reaction vessels having recesses in a second glass plate, the etching of the second glass plate is performed, e.g., for a period of time sufficient to achieve a desired depth of the recesses spaced from the second surface in the glass volume of the second glass plate, or is etched only for a period of time after which the second glass plate still has a closed second surface. Optionally, therein, the bottom of the reaction vessels may have concave recesses that have a parabolic or conical cross-section. Such concave recesses may be formed at any position onto which a laser beam has been irradiated in a punctiform manner. Preferably, such concave recesses have a cross-sectional opening and a depth of a few micrometers, e.g., 1 to 5 μm.

The embodiment in which the second plate has second recesses is particularly suitable for use of the recesses in the first plate as culture vessels for cells, in particular human or animal cells. In a method for culturing cells in the recesses, a liquid, e.g. cultivation medium and/or reagents to be tested, may be moved through the second recesses, e.g. introduced into or discharged from the recesses of the first glass plate. E.g. a cell suspension in medium can be filled into the recesses of the first glass plate from a direction opposite to the second plate or into the open cross-sectional openings of the recesses, with medium exiting through the second recesses. The cell suspension in medium may be, e.g. whole blood, or cultured cells in buffer or culture medium. This embodiment is suitable for use as a filter, e.g. for a cell suspension in medium. Therein, in the process, a medium, e.g. culture medium or buffer, may contact or be allowed to flow along the free surface of the second plate to create a medium exchange through the second recesses, e.g. to remove products of metabolism passing through the second recesses.

The invention further relates to a method of analysis in which the reaction vessels in glass are irradiated with light and light emanating from the reaction vessels is detected, and to the use of the reaction vessels made of glass in the method of analysis.

Therein, light for analysis can preferably be irradiated approximately perpendicularly onto the second plate, to the surface of the second glass plate that lies opposite to the first glass plate, or to the surface of the second glass plate facing the first glass plate.

It has shown that recesses, in particular recesses which extend conically from the first surface into the volume of the first glass plate, with their wall form a clear contrast to the bottom of the recesses when irradiated with e.g. visible light. With optical detection, therefore, the circumference of the recesses can be recorded and displayed, in particular as a dark ring in contrast to the bottom of the recesses.

Further, the invention relates to methods of analysis comprising the step of providing reaction vessels which are produced according to a production method according to the invention, or which are reaction vessels according to the invention, introducing a sample, e.g. patient sample, which may be cell-free, e.g. blood plasma, or cell-containing, e.g. whole blood or cells separated from whole blood, or tissue material, into reaction vessels, and beforehand, simultaneously or subsequently, adding at least one reagent to reaction vessels, and analyzing.

Optionally, the at least one reagent may be added, singly or sequentially multiple times, in different amounts to multiple reaction vessels. The reagent may be, e.g., a pharmaceutical agent, and the analyzing may comprise measuring the effect of the agent on the sample. Optionally, the method may comprise one or more incubation steps, e.g., under cell culture conditions (37° C., 5% $CO_2$ atmosphere, quiescent or with agitation).

Analyzing can be an optical measurement of the reaction vessels, e.g. during or after sequencing of DNA and/or RNA and/or of protein in the reaction vessels after addition of reagents for sequencing, optionally after lysis of cells, or the determination of proteins, e.g. after reaction with a binding molecule added as a reagent, e.g. an antibody, which is preferably labeled with a dye. Preferably, for samples containing cells, e.g. the analyzing comprises determining the transcribed RNAs and/or the translated proteins, in particular for samples to which no agent was added compared to samples to which agent was added. Optionally, the method of analysis may comprise removing a portion of the sample from a reaction vessel, further optionally introducing the removed sample portion into another reaction vessel according to the invention or produced according to the invention. The addition of sample and/or reagent to the reaction vessels can be performed, e.g. by moving liquid drops of the sample and/or liquid drops of the reagent, wherein the liquid drops are produced and moved, e.g. as part of a liquid jet, such as by exposure to electromagnetic radiation, by exposure to sound or ultrasound, by application of an electric field, or by application of pressure. The generation of liquid droplets is known as inkjet printing process or pipetting. Alternatively, laser-based printing processes, e.g. laser transfer printing, can be used. Preferably, the addition of sample and/or of reagent is performed without contact of the dosing device with the reaction vessel.

In embodiments in which strip conductors are disposed at the recesses, methods of analysis may involve applying voltage to the interior volume of the recesses and measuring electrical parameters present in the interior volume between the strip conductors.

The figures schematically show in

Figure 2:
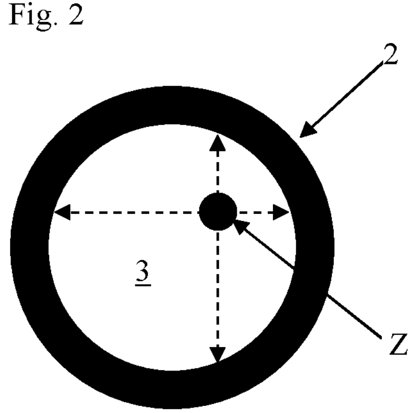
Figure 3:
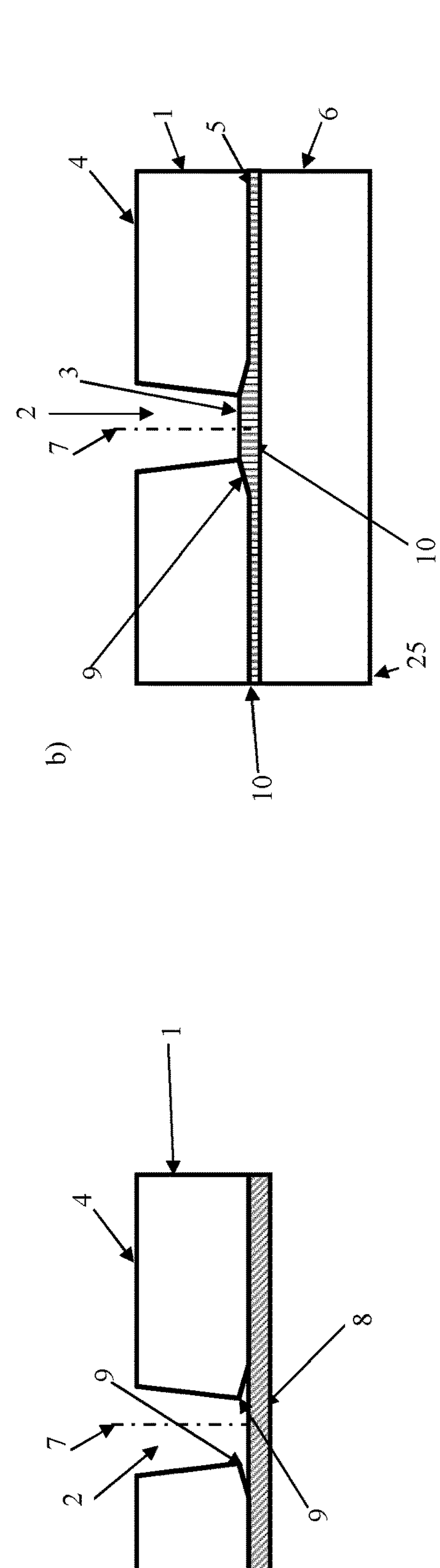
Figure 4:
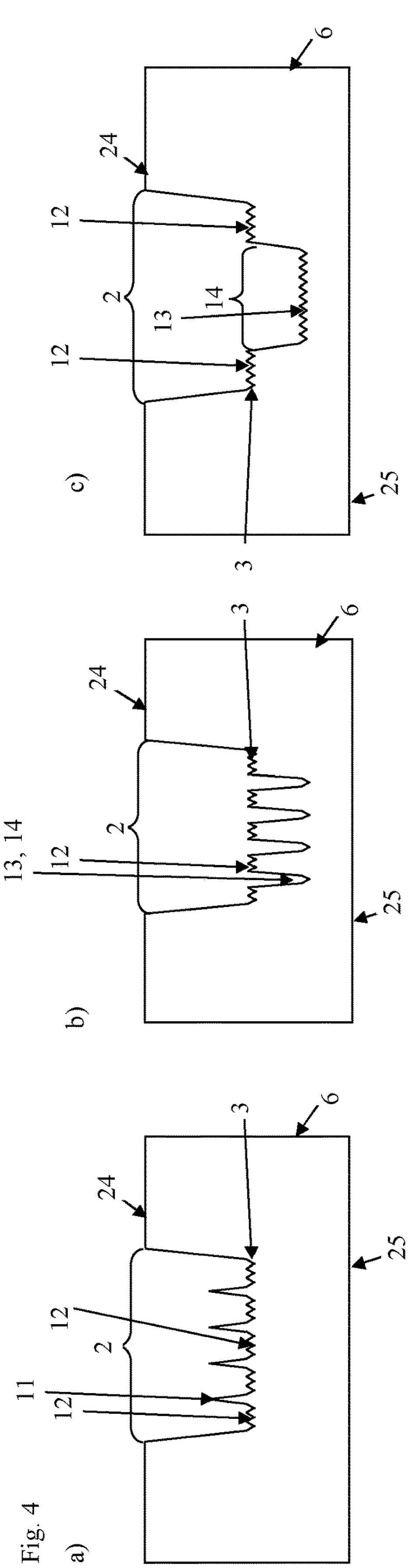
Figures 5, 6:
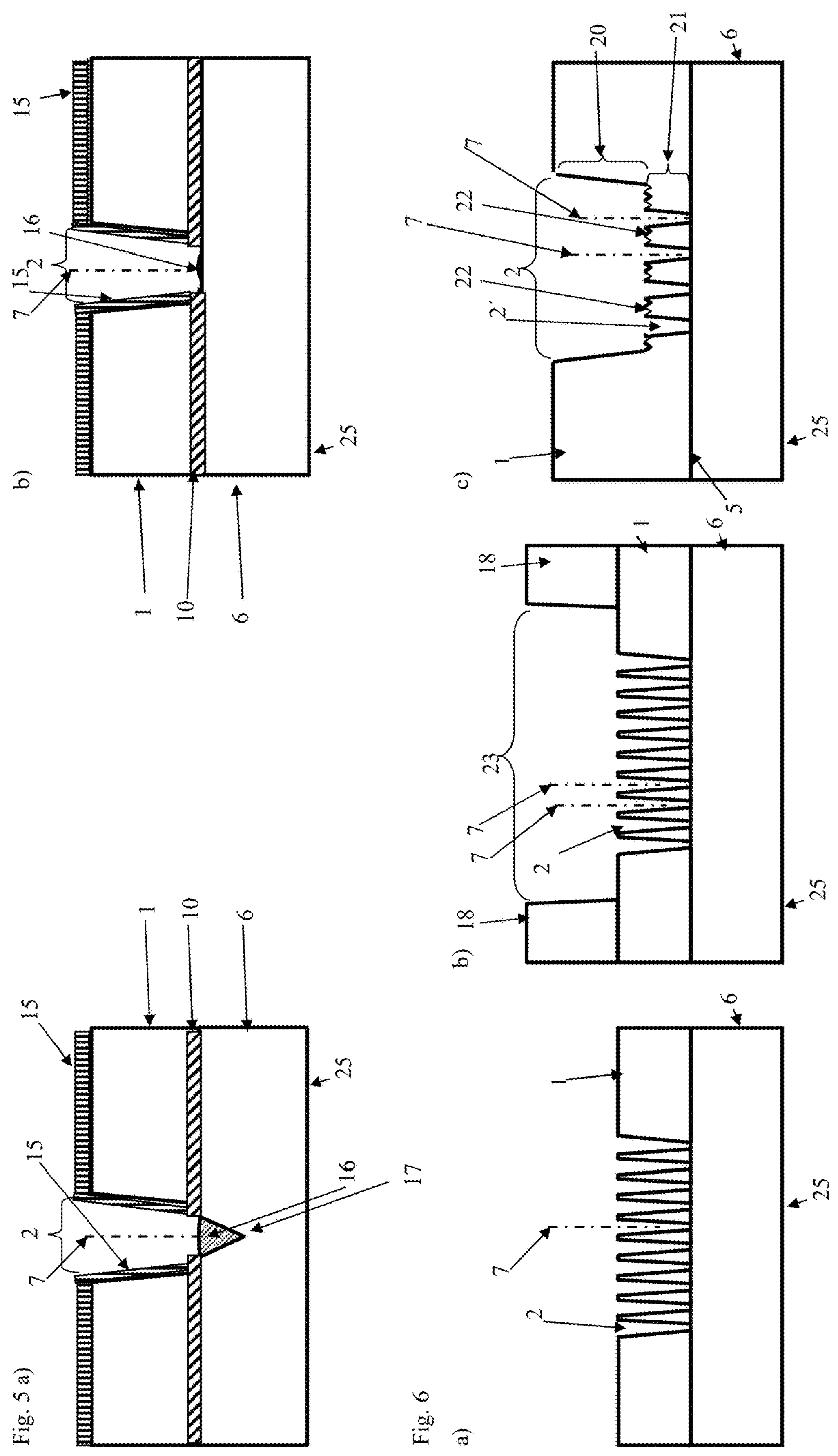
Figure 7:
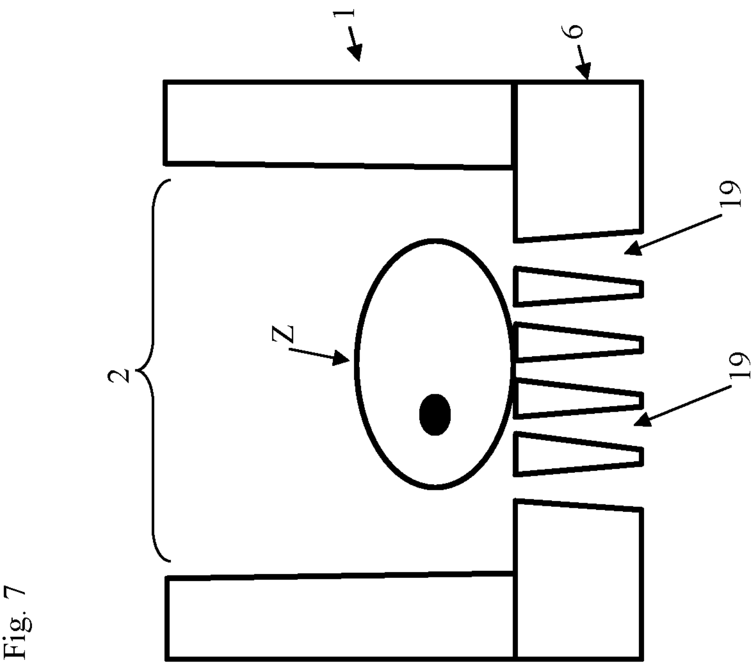

FIG. 1 in cross-section perpendicular to the surface of the first glass plate, an embodiment of the reaction vessels in glass made of two glass plates, FIG. 2 in top view of the first surface of the first glass plate the optical analysis of a reaction vessel produced according to the invention, FIG. 3*a*) and *b*) another embodiment in cross-section perpendicular to the surface of the first glass plate, FIG. 4*a*), *b*), *c*) embodiments in cross-section perpendicular to the surface of the second glass plate, FIG. 5*a*)-*b*) embodiments with strip conductors in cross-section perpendicular to the surface of the first glass plate, FIG. 6*a*)-*c*) further multi-part embodiments in cross-section perpendicular to the surface of the first glass plate, and in FIG. 7 another embodiment in cross-section perpendicular to the surface of the first glass plate.

FIG. 1 shows a first glass plate 1 in which the recess 2 extends through the full thickness and the bottom 3 is formed by a second glass plate 6 tightly connected to the second surface 5 of the first glass plate 1.

FIG. 2 shows, in top view of a first glass plate 1, a recess 2 whose wall forms a strong optical contrast with the bottom 3, so that the wall is clearly shown as a circumferential boundary of the bottom 3. Under illumination directed through the bottom 3, a particle, e.g. a biological cell Z, can be seen with good contrast against the bottom 3, especially when the cell Z is marked by a dye, e.g. a fluorescent dye.

FIG. 3*a*) shows a first glass plate 1, the second surface 5 of which is coated over its entire surface with etch resist 8, e.g. a plastic film with a UV-soluble adhesive, after irradiation of a laser pulse perpendicular onto the glass plate 1 and subsequent etching. The etching creates the recess 2 symmetrically about the light path of the laser pulse so that the longitudinal central axis 7 extends along the original light path of the laser pulse. The etching starts from the first surface 4 and creates a frustoconical recess 2 that extends to the etch resist 8. A chamfer or undercut 9 is created around the recess 2 along the second surface or between the second surface 5 and the etch resist 8.

FIG. 3*b*) shows glass vessels formed as recesses 2 in a first glass plate 1 and extending through the full thickness of the first glass plate 1. The bottom 3 of the recess is formed by glass frit 10, which is applied to completely cover the surface of the second plate 6 and also fills the area of the chamfer 9.

FIG. 4 shows embodiments of each of a recess 2 formed as a single piece in a second glass plate 6. This shows that irradiating laser pulses onto the first surface 24 of the second glass plate at a plurality of positions spaced apart by, e.g. 1 to 10 μm and therefore forming a location, at which exactly one recess 2 is produced by etching. Therein, a concave recess 12 may be formed by the etching at each position 12 on the bottom 3 of the recess 2.

As shown in FIG. 4*a*), a glass tip 11 projecting in perpendicular to the first surface 24 from the bottom 3 into the recess 2 is produced during etching if at least 3 positions 12 onto which laser pulses are irradiated are arranged at a greater spacing, e.g. at a distance of 20 μm. Therein, each position 12 onto which a laser pulse was irradiated, during etching results in a concave recess in the bottom 3.

FIG. 4*b*) shows that laser pulses irradiated at individual positions 13 and penetrating deeper into the thickness of the second glass plate 6 form further recesses 14 there during etching, which extend deeper into the second glass plate 6 than the recess in other positions 12 where laser pulses were irradiated to a lesser depth into the second glass plate 6. The depth of penetration of the laser pulses into the second glass plate 6 can be predetermined by adjusting the focus position and/or the strength of the pulse energy of the laser pulses.

FIG. 4*c*) shows that irradiating laser pulses penetrating deeper into the second glass plate 6 at positions 13 arranged alongside each other during etching form another recess 14 there extending deeper into the thickness of the second glass plate 6 than the recess whose bottom 3 is formed during etching from other positions 12 in which the laser pulses have been irradiated less deeply into the second glass plate 6.

FIGS. 5*a*) and *b*) show embodiments in which a first strip conductor 15 is applied to the first glass plate 1, in this case to its first surface 4, and the second plate 6 has a second strip conductor 16 lying thereon on its surface, which is flat and faces the first glass plate 1. The first strip conductor 15 and the second strip conductor 16 may be applied, e.g. by sputtering, printing or by chemical or galvanic deposition or combinations thereof. One of the first and second strip conductors 15, 16 may be applied over the entire surface, and the other strip conductor 15, 16 may be formed in the form of spaced apart tracks which traverse the cross-section of the recess 2. The layer of glass frit 10 disposed between the first glass plate 1 and the second plate 6 and solidified after softening connects these two plates 1, 6 and spaces the first strip conductor 15 from the second strip conductor 16 so that these strip conductors contact a liquid contained in the recess 2 at a distance from each other. Optionally, in general, the layer of glass frit 10 may be disposed solely between the first glass plate 1 and the second plate 6 and leave the area of the recesses 2 exposed, or the layer of glass frit 10 may extend across the thickness of the layer of the first strip conductor 15 into the recess 2 to within a distance of the second strip conductor 16 or to adjacent the second strip conductor 16.

FIG. 5*a*) shows an embodiment in which the second strip conductor 16 runs in ditches 17 formed as recesses in the second plate 6, preferably by irradiation with laser pulses along the course of the ditches with subsequent etching.

FIG. 5*b*) shows an embodiment in which the second strip conductor 16 is arranged on the flat surface of the second plate 6.

FIG. 6*a*) shows the arrangement of at least two, presently depicted ten, recesses 2, the longitudinal central axes 7 of which are arranged at equal distances from one another. The recesses 2 are enclosed by walls which extend through the entire thickness of the first glass plate 1. Therein, the recesses 2 taper from the first surface 4 to the second surface 5 of the first glass plate 1. The cross-sectional openings of the recesses 2 are covered by the second plate 6 in the plane of the second surface 5.

FIG. 6*b*) shows an embodiment in which a third plate 18 is connected to the first surface 4 of the first glass plate 1, wherein the third plate 18 having third recesses 23 extending through its thickness and covering at least two, in FIG. 7 b) ten, recesses 2 formed in the first glass plate 1. The distance between the longitudinal central axes of the recesses 2 in the first glass plate may be, e.g. 10 to 100 μm.

FIG. 6*c*) shows an embodiment in which a recess is produced in the first glass plate 1 by etching after the first glass plate 1 has been irradiated with laser pulses passing through its full thickness at the locations where partial recesses 2' are formed, and has been irradiated therebetween with laser pulses extending maximally over an upper thickness section 20. The upper thickness section 20 extends from the first surface 4 of the first glass plate 1 to adjacent to the partial recesses 2', leaving partial walls 22 between the partial recesses 2' at the locations where laser pulses were irradiated maximally to the depth of the upper thickness section 20. The terminal cross-sectional openings of the partial recesses 2', which are opposite to the first thickness section 20, are covered by a second plate 6, which is connected to the first plate 1.

FIG. 7 shows an embodiment in which the second plate 6 has second recesses 19 in the area of the recesses 2 formed in the first glass plate 1. The second recesses 19 may optionally extend only into a portion of the thickness of the second plate 6, or may extend through the full thickness of the second plate 6, as shown here. The second recesses have diameters in the plane of the surface of the second plate 6 joined to the first glass plate 1 that are smaller than the diameter of a cell Z by a factor of 5 to 10, e.g. A second plate 6 with second recesses 19 extending through its full thickness form a retaining device for larger particles, e.g. a cell Z.

According to a preferred embodiment, in FIG. 7 the second recesses 19 taper and have their smaller diameter in the plane of the surface of the second plate 6 facing the first glass plate.

LIST OF REFERENCE SIGNS

1 first glass plate 14 further recess
2 recess 15 first strip conductor
2' partial recess 16 second strip conductor
3 bottom 17 ditch
4 first surface 18 third plate
5 second surface 19 second recess
6 second plate 20 upper, first thickness section
7 longitudinal central axis 21 lower, second thickness section
8 etch resist 22 partial walls
9 chamfer, undercut 23 third recess
10 glass frit 24 first surface of the second plate
11 glass tip 25 second surface of the second plate
12 position of irradiated laser pulse Z cell
13 position of more deeply irradiated laser pulse

The invention claimed is:

1. A method of producing a plurality of glass reaction vessels formed as recesses in a first glass plate, comprising the steps of irradiating punctiform laser pulses of a wavelength for which the first glass plate is transparent onto locations of a first surface of the first glass plate at which each of the recesses is to be formed, wherein punctiform irradiated laser beams are arranged in the plane of the first surface of the first glass plate at a distance of exactly a diameter of one of the reaction vessels plus a thickness of a wall between the reaction vessels, wherein the irradiating comprises irradiating a laser beam along a circumferentially closed path at the locations and the circumferentially closed path is formed by laser beam pulses irradiated side by side, etching the first glass plate for a period of time sufficient to create the recesses at the locations, the etching being performed until the recesses have a depth extending through a full thickness of the first glass plate, wherein the first glass plate is subjected to etching without a mask and without etch resist, connecting a second plate to a second surface of the first glass plate, wherein during connecting, the second plate is arranged against the second surface of the first glass plate opposite to the first surface of the first glass plate, wherein the connecting is performed by placing the second surface of the first glass plate directly against the second plate and conducting heating or by anodic bonding of the second surface of the first glass plate to the second plate.

2. The method according to claim 1, wherein the depth of the recesses is at least 30 μm.

3. The method according to claim 1, wherein the recesses have a depth to diameter aspect ratio of at least 2.

4. The method according to claim 1, wherein the second plate consists of glass, silicon, sapphire, ceramic, metal or a combination of at least two layers thereof.

5. The method according to claim 1, wherein the laser pulses are irradiated at a plurality of spaced-apart positions at the locations.

6. The method according to claim 5, wherein at a first share of the positions laser pulses are irradiated into the first glass plate up to a first thickness section, and at a second share of the positions laser pulses are irradiated deeper than at the first share of the positions into the first glass plate up to an adjacent second thickness section, wherein during etching the recesses are formed including recesses extending over the first thickness section and partial recesses spaced by partial walls and extending over the second thickness section.

7. The method according to claim 6, wherein some of the positions are arranged at a distance of at most 10 μm, wherein at least three of the positions are spaced at least 20 μm apart.

8. The method according to claim 1, wherein a focal position of the laser pulses is adjusted such that laser pulses penetrate into the first glass plate only up to a thickness section which does not extend over the entire thickness of the first glass plate.

9. The method according to claim 1, comprising connecting a third plate having third recesses extending through its full thickness to the first surface of the first glass plate with the third recesses matching the recesses of the first glass plate.

10. The method according to claim 1, wherein the second plate comprises second recesses and the connecting comprises connecting the second plate to the first glass plate with its second recesses adjacent to the recesses of the first glass plate.

11. A method of producing a plurality of glass reaction vessels formed as recesses in a first glass plate, comprising the steps of irradiating punctiform laser pulses of a wavelength for which the first glass plate is transparent onto locations of a first surface of the first glass plate at which each of the recesses is to be formed, wherein punctiform irradiated laser beams are arranged in the plane of the first surface of the first glass plate at a distance of exactly a diameter of one of the reaction vessels plus a thickness of a wall between the reaction vessels, etching the first glass plate for a period of time sufficient to create the recesses at the locations, the etching being performed until the recesses have a depth extending through a full thickness of the first glass plate, wherein the first glass plate is subjected to etching without a mask and without etch resist, applying a first strip conductor to the first surface of the first glass plate opposite to the second plate, and applying second strip conductors to a surface of the second plate facing the first glass plate;

connecting a second plate to a second surface of the first glass plate, wherein during connecting, the second plate is arranged against the second surface of the first glass plate opposite to the first surface of the first glass plate, wherein the connecting is performed by placing the second surface of the first glass plate directly against the second plate and conducting heating or by anodic bonding of the second surface of the first glass plate to the second plate.

12. The method according to claim 11, comprising irradiating a laser beam along a circumferentially closed path at the locations.

13. The method according to claim 12, wherein the circumferentially closed path is formed by laser beam pulses irradiated side by side.

14. The method according to claim 11, wherein the second plate comprises ditches and the second strip conductors are applied in the ditches.

15. A method of producing a plurality of glass reaction vessels formed as recesses in a first glass plate, comprising the steps of irradiating punctiform laser pulses of a wavelength for which the first glass plate is transparent onto locations of a first surface of the first glass plate at which each of the recesses is to be formed, wherein punctiform irradiated laser beams are arranged in the plane of the first surface of the first glass plate at a distance of exactly a diameter of one of the reaction vessels plus a thickness of a wall between the reaction vessels, etching the first glass plate for a period of time sufficient to create the recesses at the locations, the etching being performed until the recesses have a depth extending through a full thickness of the first glass plate, wherein the first glass plate is subjected to etching without a mask and without etch resist, applying strip conductors on the first glass plate such that the strip conductors cover at least a section of an inner wall of the recesses connecting a second plate to a second surface of the first glass plate, wherein during connecting, the second plate is arranged against the second surface of the first glass plate opposite to the first surface of the first glass plate, wherein the connecting is performed by placing the second surface of the first glass plate directly against the second plate and conducting heating or by anodic bonding of the second surface of the first glass plate to the second plate.

* * * * *